(12) United States Patent
Jiang et al.

(10) Patent No.: US 10,149,471 B2
(45) Date of Patent: Dec. 11, 2018

(54) DISINFECTANT COMPOSITION HAVING RESIDUAL BIOCIDAL PROPERTIES

(71) Applicant: Lonza Inc., Allendale, NJ (US)

(72) Inventors: Xiao Jiang, Montvale, NJ (US); Joseph Kimler, Yardville, NJ (US); Milady Brutofsky, Cumming, GA (US)

(73) Assignee: Lonza Inc., Morristown, NJ (US)

( * ) Notice: Subject to any disclaimer, the term of this patent is extended or adjusted under 35 U.S.C. 154(b) by 0 days.

(21) Appl. No.: 15/809,097

(22) Filed: Nov. 10, 2017

(65) Prior Publication Data

US 2018/0132481 A1    May 17, 2018

Related U.S. Application Data

(60) Provisional application No. 62/420,887, filed on Nov. 11, 2016.

(51) Int. Cl.
| | | |
|---|---|---|
| *A61K 31/155* | (2006.01) | |
| *A01N 33/04* | (2006.01) | |
| *A01N 25/00* | (2006.01) | |
| *A01N 25/02* | (2006.01) | |
| *A01N 47/44* | (2006.01) | |

(52) U.S. Cl.
CPC ............. *A01N 33/04* (2013.01); *A01N 25/00* (2013.01); *A01N 25/02* (2013.01); *A01N 47/44* (2013.01)

(58) Field of Classification Search
USPC ........................................................ 514/635
See application file for complete search history.

(56) References Cited

U.S. PATENT DOCUMENTS

| | | |
|---|---|---|
| 5,492,650 A | 2/1996 | Lang et al. |
| 5,547,662 A | 8/1996 | Khan et al. |
| 5,641,498 A | 6/1997 | Loosemore |
| 5,763,412 A | 6/1998 | Khan et al. |
| 6,121,224 A | 9/2000 | Fonsny et al. |
| 6,159,924 A | 12/2000 | Weller et al. |
| 6,281,178 B1 | 8/2001 | Ryklin et al. |
| 7,148,187 B1 | 12/2006 | Simon et al. |
| 7,217,759 B2 | 5/2007 | Hodge et al. |
| 7,345,015 B1 | 3/2008 | Kong et al. |
| 7,414,017 B2 | 8/2008 | Kong et al. |
| 7,598,214 B2 | 10/2009 | Cusack et al. |
| 7,807,616 B2 | 10/2010 | Meine et al. |
| 7,888,404 B2 | 2/2011 | Kritzler |
| 8,003,593 B2 | 8/2011 | Schwarz et al. |
| 8,980,818 B2 | 3/2015 | Wates et al. |
| 9,096,821 B1 | 8/2015 | Hope et al. |
| 2002/0039979 A1 | 4/2002 | Aszman et al. |
| 2003/0100465 A1 | 5/2003 | Kilkenny et al. |
| 2008/0010772 A1 | 1/2008 | Kong et al. |
| 2010/0240799 A1* | 9/2010 | Hofmann ................. A61K 8/43 523/122 |
| 2012/0171300 A1 | 7/2012 | Koenig et al. |
| 2014/0171512 A1 | 6/2014 | Kloeppel et al. |
| 2015/0314471 A1 | 11/2015 | Thompson et al. |

FOREIGN PATENT DOCUMENTS

| | | |
|---|---|---|
| DE | 102006051560 | 5/2008 |
| EP | 0333143 | 9/1989 |
| EP | 0343605 | 11/1989 |
| EP | 0898611 | 5/2001 |

OTHER PUBLICATIONS

PCT/US2017/061049 International Search Report and Written Opinion dated Jan. 2, 2018.
Co-Pending U.S. Appl. No. 15/715,371, filed Sep. 26, 2017.

* cited by examiner

*Primary Examiner* — Rei Tsang Shiao
(74) *Attorney, Agent, or Firm* — Dority & Manning, P.A.

(57) ABSTRACT

A composition having biocidal properties is disclosed. The composition includes a biocide in combination with a film forming component. In one embodiment, for instance, the biocide comprises an amine while the film forming component comprises one or more polyvinyl alcohol polymers. The disinfectant composition forms a film on a surface that is abrasion resistant and will provide biocidal activity over an extended period of time, while being completely water dispersible.

24 Claims, No Drawings

DISINFECTANT COMPOSITION HAVING RESIDUAL BIOCIDAL PROPERTIES

RELATED APPLICATIONS

The present application is based on and claims priority to U.S. Provisional Patent application Ser. No. 62/420,887, which was filed on Nov. 11, 2016, and which is incorporated herein by reference.

BACKGROUND

A disinfectant refers to any chemical agent capable of killing, destroying, or inhibiting the growth of organisms, particularly microorganisms. Disinfectant products include hard surface cleaners, hand sanitizers, pre-disinfectant cleaners for instruments, sterilizing and high-level disinfectant compositions, and the like.

Ideally, a disinfectant has broad-spectrum activity against all types of microorganisms at various pH levels. The disinfectant should also have high efficacy so that a minimum amount of the anti-microbial agent can be used to save cost and to avoid or reduce any possible adverse effects caused by the anti-microbial agent. Also, it is desirable that the disinfectant is stable to any changes in temperature encountered during manufacturing, packaging, and shipping as well as during storage. Further, an ideal disinfectant is physically and chemically compatible with ingredients of different application systems so that the anti-microbial agent can suitably be incorporated in various products.

In the past, various different disinfectants have been suggested. For example, disinfectants that have been used in the past include alcohols such as isopropyl alcohol and ethanol, copper compounds, silver compounds, aldehydes, oxidizing agents such as sodium hypochlorite, and the like.

Most disinfectant compositions that are commercially available are well suited to killing microorganisms on surfaces when applied. The efficacy of many disinfectant compositions, however, rapidly decreases after application. In particular, the disinfectant composition fails to remain on the surface for any length of time to provide a sustained efficacy. The disinfectant composition either rapidly degrades, evaporates, or tends to be physically removed from the surface due to repeated touching or wiping with a cloth. As a result, if the surface becomes re-contaminated, the disinfectant composition must be reapplied in order to kill the newly deposited microorganisms.

In view of the above, a need exists for a disinfectant composition that delivers fast initial antimicrobial kill and also provides residual protection and long lasting efficacy. A need also exists for a disinfectant composition capable of providing prolonged antimicrobial activity against microorganisms without discoloring a surface or making the surface sticky to the touch. A need also exists for a disinfectant composition that provides prolonged efficacy against microorganisms without creating chemical build up on the surface.

SUMMARY

In general, the present disclosure is directed to a composition having biocidal properties. More particularly, the present disclosure is directed to a disinfectant composition that displays efficacy over an extended length of time. The disinfectant composition has prolonged antimicrobial properties without causing chemical build up on an adjacent surface.

In one embodiment, the present disclosure is directed to a composition for disinfecting surfaces that comprises at least one biocide. The biocide, for instance, can comprise an amine, a chlorhexidine, a biguanide, or mixtures thereof. In one particular embodiment, one or all of the above biocides may also be used in combination with a quaternary ammonium cation. In accordance with the present disclosure, the at least one biocide is combined with a film forming component. The film forming component, for instance, may comprise a polyvinyl alcohol, a polyvinyl pyrrolidone, a glycol such as polyethylene glycol, or mixtures thereof. The biocide and the film forming component are combined together and blended with a liquid carrier. The liquid carrier, for instance, may comprise water. Water can be present in the composition, for instance, in an amount greater than about 40% by weight, such as in an amount greater than about 50% by weight, such as in an amount greater than about 60% by weight, such as in an amount greater than about 70% by weight.

In one embodiment, the biocide contained in the composition comprises an amine, particularly a tertiary amine. For instance, the biocide may comprise a tertiary alkyl amine, such as an alkyl amine having from about 8 to about 16 carbon atoms. Examples of amine biocides that may be used in the composition include N,N-bis(3-aminopropyl) dodecylamine, N-(3-aminopropyl)-N-dodecylpropane-1,3-diamine, N-(3-aminopropyl)-N-decyl-1,3-propanediamine, N-(3-aminopropyl)-N-tetradecyl-1,3-propanediamine, or mixtures thereof.

The at least one biocide can be present in the composition in an amount from about 0.1% to about 2% by weight, such as from about 0.2% to about 2.0% by weight, such as from about 0.3% to about 1.5% by weight.

In one embodiment, the film forming component includes a polyvinyl alcohol alone or in combination with another film forming component. The polyvinyl alcohol, for instance, can have a degree of hydrolysis of at least about 80 mol %, such as at least about 90 mol %, such as at least about 95 mol %, such as at least about 97 mol %.

In one embodiment, the composition contains a first polyvinyl alcohol and a second polyvinyl alcohol. The first polyvinyl alcohol can have a degree of hydrolysis greater than the degree of hydrolysis of the second polyvinyl alcohol. For instance, in one embodiment, the first polyvinyl alcohol can have a degree of hydrolysis of about 98 mol %. The second polyvinyl alcohol, on the other hand, can have a degree of hydrolysis of from about 90 mol % to about 97 mol %, such as about 96 mol %. The first polyvinyl alcohol can be present in the composition in relation to the second polyvinyl alcohol at a weight ratio of from about 1:1 to about 4:1, such as from about 1.5:1 to about 3:1.

The total amount of film forming components contained in the composition can generally be from about 1% to about 10% by weight, such as in an amount from about 2% to about 8% by weight, such as in an amount from about 3% to about 7% by weight.

In one embodiment, the composition can further contain an evaporating agent. The evaporating agent can have a boiling point of less than about 90° C., such as less than about 85° C., at 1 ATM. For example, the evaporating agent may comprise an alcohol, such as isopropyl alcohol.

The composition may contain various other components and ingredients. For instance, the composition can also contain a chelating agent and/or a surfactant. The surfactant may comprise, for instance, an alkoxylated alcohol.

The disinfectant composition of the present disclosure can be applied to a surface using any suitable method. For instance, the composition can be sprayed or otherwise applied to a surface. In one embodiment, a disposable substrate can be pre-impregnated with the composition to form a pre-moistened wipe.

Other features and aspects of the present disclosure are discussed in greater detail below.

DETAILED DESCRIPTION

It is to be understood by one of ordinary skill in the art that the present discussion is a description of exemplary embodiments only, and is not intended as limiting the broader aspects of the present disclosure.

The present disclosure is generally directed to a composition for disinfecting surfaces. More particularly, the present disclosure is directed to disinfecting compositions that not only deliver fast initial antimicrobial kill over a broad spectrum of microorganisms, but also provide residual antimicrobial activity over an extended length of time. In general, the composition contains at least one biocide in conjunction with a film forming component. The film forming component synergistically works in conjunction with the biocide to not only kill a broad spectrum of microorganisms initially but also forms a light coating or film over the surface providing antimicrobial properties over an extended length of time. Of particular advantage, the thin coating or film formed on the surface is clear, non-tacky, and relatively invisible. The dried disinfectant composition can also be re-dissolved in water or in further applications of the disinfectant composition. In this manner, the disinfectant composition is resistant to chemical build up over time allowing for repeated use of the composition on the same surface.

The disinfectant composition can be used in any suitable industry or field. For instance, the disinfectant composition can be used in the food and beverage field. The disinfectant composition, for instance, may comprise a hard surface disinfectant, a hand sanitizer, a sterilizing or high-level disinfectant composition, a pre-disinfectant cleaner for instruments and the like.

As described above, disinfectant composition of the present disclosure contains at least one biocide in combination with a film forming component. The biocide and film forming component can be selected so as to maximize antimicrobial activity and in order to maximize the longevity of the activity. In one embodiment, the at least one biocide may comprise an amine with biocidal properties, a chlorhexidine, a biguanide, or mixtures thereof.

Suitable amines include, but are not limited to, tertiary amines, such as ($C_8$-$C_{16}$) alkyl amines. The term "($C_8$-$C_{16}$) alkyl amine" encompasses all amines which contain a ($C_1$-$C_{16}$) alkyl group. One ($C_8$-$C_{16}$) alkyl amine is N,N-bis(3-aminopropyl)dodecylamine, available as Lonzabac® 12.30 and 12.100 from Lonza, Inc.

Other exemplary tertiary amines include, for example, N-(3-aminopropyl)-N-dodecyl propane-1,3-diamine, N-(3-aminopropyl)-N-decyl-1,3-propanediamine, N-(3-aminopropyl)-N-tetradecyl-1,3-propanediamine as well as their acid addition compounds. Other similar tertiary amines may be used In one embodiment, the biocide may comprise a polymeric biguanide, otherwise known as a polybiguanide, or a salt, analog, or derivative thereof. In one embodiment, the polybiguanide may be a copolymer or a heteropolymer. The polybiguanide may be linear, branched, circular, and/or dendrimeric. The number of polymer repeating units can vary from 2 to 1,000, such as from 5 to 750, such as from 10 to 500, such as from 25 to 250, such as from 50 to 100 repeating units. In one specific embodiment, the polybiguanide may comprise polyhexamethylene biguanide (PHMB), polyhexamethylene monoguanide (PHMG), polyethylene biguanide (PEB), polytetramethylene biguanide (PTMB), polyethylene hexamethylene biguanide (PHMB), polymethylene biguanides (PMBs), poly(allylbiguanidnio-co-allyamine, poly(N-vinyl-biguanide), polyallylbiguanide etc.

For example, in one particular embodiment, the biocide may comprise a polyalkylene biguanide, such as polyhexamethylene biguanide. In one embodiment, the biocide may comprise polyhexamethylene biguanide hydrochloride (PHMB), also known as polyaminopropyl biguanide (PABP).

PHMB is commonly represented by the following formula, though it is known to exist as a complex mixture of polymeric biguanides with various terminal groups including guanidine (not shown).

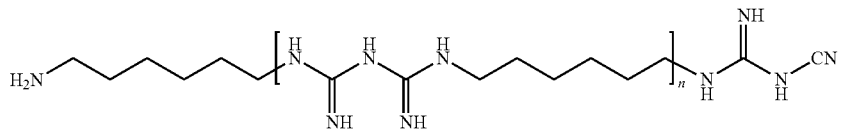

The value n represents the number of repeating units of the biguanide polymer.

More particularly, PHMB can be a mixture of various biguanide polymers that can include different combinations of terminal groups, e.g., amine, cyanoguanidino, and guanidine. Based only on these three terminal groups, at least six possible biguanide polymers can exist. There can be one biguanide polymer with two terminal amine groups, which is referred to as PHMB-AA, one with two terminal cyanoguanidino groups, which is referred to as PHMB-CGCG, and one with two terminal guanidine groups, which is referred to as PHMB-GG (see, below). There are also the three possible biguanide polymers having a combination of two different terminal groups. Again, based on the above terminal groups they include amine-cyanoguanidino (PHMB-ACG), amine-guanidino (PHMB-AG) and guanidine-cyanoguanidino (GCG). Accordingly, a sample of PHMB may comprise a mixture of polymeric biguanides with the three mentioned terminal groups. Moreover, some of the composition can include in-chain polymeric guanide (not shown). The subscript "n" represents the average number of repeating groups, and a distribution of polymer length exists for each of the polymers shown below.

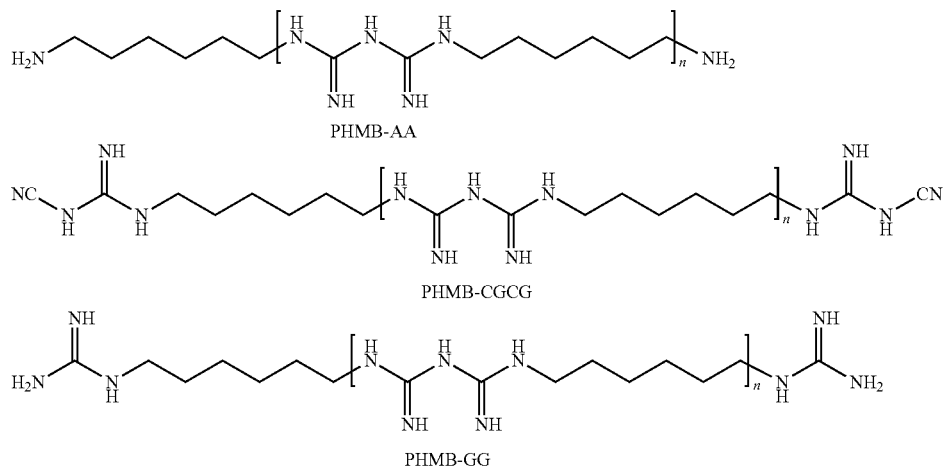

PHMB-AA

PHMB-CGCG

PHMB-GG wherein n can be from about 1 to about 50, such as from about 1 to about 20.

Polyhexamethylene biguanide, such as polyhexamethylene biguanide hydrochloride, has a broad antimicrobial range and is fast acting. Further, the antimicrobial agent is stable over a broad pH range.

In still another embodiment, the biocide may comprise a chlorhexidine or derivatives or salts thereof. Chlorhexidine is commonly represented by the following formula.

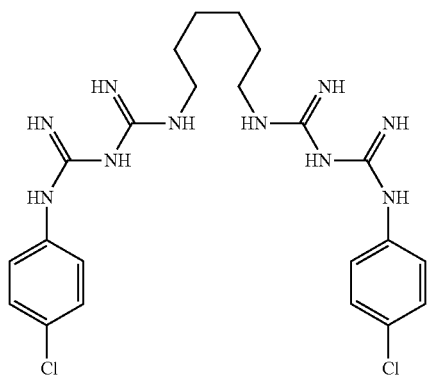 [SMILES: N=C(NCCCCCCNC(=N)NC(=N)Nc1ccc(Cl)cc1)NC(=N)Nc1ccc(Cl)cc1]

In one embodiment the biocide may comprise a chlorhexidine salt. For example, the biocide may comprise chlorhexidine gluconate, chlorhexidine hydrochloride, or chlorhexidine acetate.

One or more of the above biocides is generally present in the disinfectant composition in an amount greater than about 0.1% by weight, such as in an amount greater than about 0.2% by weight, such as in an amount greater than about 0.3% by weight. The one or more biocides is generally present in an amount less than about 4% by weight, such as in an amount less than about 2% by weight, such as in an amount less than about 1% by weight, such as in an amount less than about 0.8% by weight, such as in an amount less than about 0.5% by weight.

In one embodiment, the disinfectant composition can be sold in a concentrated form and then later diluted prior to use. In the concentrated form, the one or more biocides may be present in the composition in an amount greater than about 0.2% by weight, such as in an amount greater than about 0.4% by weight, such as in an amount greater than about 0.6% by weight. In the concentrated composition, the one or more biocides are generally present in an amount less than about 4% by weight, such as in an amount less than about 3% by weight.

In one embodiment, in addition to one of the biocides described above or a mixture of the above biocides, the composition may contain a quaternary ammonium cation. The quaternary ammonium cation, for instance, may comprise a carbon/bicarbonate, halide, or propionate salt of a quaternary ammonium cation. If included in the composition, the quaternary ammonium cation is present in relatively small amounts such as less than about 0.5% by weight, such as less than about 0.3% by weight, such as in an amount of less than 0.1% by weight.

In accordance with the present disclosure, one or more biocides are combined with a film forming component to form the disinfectant composition. The film forming component generally comprises a film forming polymer capable of forming a film on a surface or otherwise extending the active life of the biocide without adversely interfering with the activity of the biocide. The film forming component, in one embodiment, has a water solubility that prevents the composition from chemical build up over prolonged and repeated use. A film forming component can also be selected that does not produce a sticky or tacky composition when combined with the biocide. Film forming components that may be incorporated into the composition, for instance, include a polyvinyl alcohol, a polyvinyl pyrrolidone, a polyalkylene glycol, a polyethyloxazoline, or mixtures thereof.

The polyvinyl alcohols that may be used in the composition of the present disclosure include polyvinyl alcohols that are at least partially hydrolyzed or fully hydrolyzed. The degree of hydrolysis of the polyvinyl alcohol polymer, for instance, is generally greater than about 80 mol %, such as greater than 90 mol %, such as greater than 93 mol %, such as greater than about 95 mol %, such as greater than about 97 mol %. In one embodiment, for instance, the disinfectant composition contains a polyvinyl alcohol polymer having a degree of hydrolysis of about 98 mol % or greater.

In one particular embodiment, the disinfectant composition can include a first polyvinyl alcohol polymer in combination with a second polyvinyl alcohol polymer. The first polyvinyl alcohol polymer can have a degree of hydrolysis greater than the second polyvinyl alcohol polymer. The first polyvinyl alcohol polymer, for instance, can be included in the composition in order to ensure that any resulting dried coating on a surface is water soluble and/or dispersible. The second polyvinyl alcohol polymer, on the other hand, can be present in amounts in order to ensure that the dried coating has longevity when applied to a surface and is resistant to any type of contact or abrasion. The first polyvinyl alcohol polymer, for instance, can have a degree of hydrolysis of generally greater than about 96 mol %, such as greater than about 97 mol %. The second polyvinyl alcohol polymer, on the other hand, can have a degree of hydrolysis of less than about 97 mol %, such as less than about 96 mol %, such as less than about 95 mol %. The degree of hydrolysis of the second polyvinyl alcohol polymer is generally greater than about 90 mol %, such as greater than about 93 mol %, such as greater than 95 mol %.

The relative amounts of the first polyvinyl alcohol polymer and second polyvinyl alcohol polymer can vary depending upon the particular application and the other components contained in the composition. In one particular embodiment, for instance the weight ratio between the first polyvinyl alcohol polymer and the second polyvinyl alcohol polymer is from about 1:1 to about 10:1, such as from about 1:1 to about 4:1, such as from about 1.5:1 to about 3:1.

In addition to polyvinyl alcohol polymers, the film forming component may also comprise a polyvinyl pyrrolidone or a polyalkylene glycol. The polyalkylene glycol, for instance, may comprise polyethylene glycol. The polyethylene glycol can generally have a number average molecular weight of greater than about 1000, such as greater than about 2000, such as greater than about 2500, such as greater than about 2800, such as greater than about 3000, such as greater than about 3200. The number average molecular weight is generally less than about 10,000, such as less than about 5000, such as less than about 4000.

One or more film forming components are generally present in the disinfectant composition in an amount greater than about 1% by weight, such as an amount greater than about 2% by weight, such as an amount greater than about 3% by weight, such as an amount greater than about 4% by weight. One or more film forming components are generally contained in the composition in an amount less than about 15% by weight, such as an amount less than about 10% by weight, such as an amount less than about 8% by weight, such as an amount less than about 7% by weight.

When the composition is sold in a concentrated form, the one or more film forming components can be present in the composition generally in an amount greater than about 4% by weight, such as an amount greater than about 6% by weight, and generally less than about 30% by weight, such as an amount less than about 25% by weight. The concentrated form, prior to use, can be diluted with one or more solvents such as water in order to arrive at the concentrations described above.

In addition to at least one biocide and at least one film forming component, the disinfectant composition can also include a liquid carrier. The liquid carrier, for instance, may comprise a polar solvent such as water or a water-miscible solvent, such as a glycol ether. The liquid carrier is generally present in the composition in an amount greater than about 40% by weight, such as an amount greater than about 50% by weight, such as an amount greater than about 60% by weight, such as an amount greater than about 70% by weight, such as an even an amount greater than about 80% by weight. In general, the liquid carrier is present in an amount less than about 97% by weight, such as an amount less than about 95% by weight, such as an amount less than about 80% by weight depending upon the particular application and formulation.

In one embodiment, the disinfectant composition can also contain an evaporating agent. The evaporating agent can be present in the composition in order to facilitate evaporation of the composition once applied to a surface. The evaporating agent, for instance, generally has a boiling point of less than liquid water. For instance, the boiling point of the evaporating agent can be less than about 90° C., such as less than about 85° C. at 1 ATM. Examples of evaporating agents include alcohols. For instance, the evaporating agent may comprise alcohols including, but not limited to, ethanol, propanol, isopropanol, and mixtures thereof. The amount of evaporating agents contained in the composition can vary widely depending upon various factors. For example the evaporating agent can be present in the composition in an amount greater than about 0.5% by weight, such as an amount greater than about 1% by weight, such as an amount greater than about 2% by weight, such as an amount greater than about 5% by weight, such as an amount greater than about 10% by weight, such as an amount greater than about 15% by weight, such as an amount greater than about 20% by weight. The evaporating agent is generally present in amount less than about 85% by weight, such as in an amount less than about 70% by weight, such as in an amount less than about 50% by weight, such as in an amount less than about 40% by weight, such as in an amount less than about 30% by weight, such as in an amount less than about 20% by weight.

In one embodiment, the disinfectant composition of the present disclosure may also contain a surfactant. Any suitable surfactant may be added to the composition including nonionic surfactants and/or cationic surfactants. The surfactant can generally be present in the composition in an amount greater than about 0.05% by weight, such as an amount greater than about 0.08% by weight. Surfactants are generally present in an amount less than about 20% by weight, such as an amount less than about 15% by weight, such as an amount less than about 10% by weight, such as an amount less than about 5% by weight, such as an amount less than about 3% by weight, such as an amount less than about 2% by weight.

In one embodiment, the disinfectant composition contains a nonionic surfactant, particularly an alkoxylated alcohol.

For example, the alkoxylated alcohol may comprise an alkoxylated fatty alcohol. The alkoxylated alcohol may have the following formula:

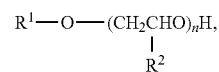

where
$R^1$ is $C_6$-$C_{18}$-alkyl or $C_6$-$C_{18}$-alkenyl,
$R^2$ is hydrogen or methyl,
and n is from 5 to 30.

In various embodiments, $R^1$ can be an $C_8$-$C_{18}$ alkyl or alkenyl group, such as a $C_9$-$C_{18}$ alkyl or alkenyl group.

For example, useful nonionic alkoxylated alcohols include, but are not limited to, alkoxylates of capryl alcohol, octanol, pelargonic alcohol, decyl alcohol, capric alcohol, undecyl alcohol, 1-undecanol, undecanol, hendecanol, lauryl alcohol, tridecyl alcohol, dodecanol, myristyl alcohol, pentadecyl alcohol, cetyl alcohol, palmitoleyl alcohol, heptadecyl alcohol, or stearyl alcohol.

The degree of alkoxylation in the surfactant can vary depending upon various factors. In one embodiment, for instance, the alkoxylated alcohol contains at least about 5 mols of alkoxylate, such as at least about 8 mols of alkoxylate, such as at least about 10 mols of alkoxylate, such as at least about 12 mols of alkoxylate, such as at least about 15 mols of alkoxylate, such as at least about 18 mols of alkoxylate, such as at least about 20 mols of alkoxylate. The degree of alkoxylation is generally less than about 80 mols, such as less than about 60 mols, such as less than about 40 mols, such as less than about 30 mols.

In one embodiment, the alkoxylated alcohol comprises an ethoxylated fatty alcohol. For example, in one particular embodiment, $R^2$ in the above formula comprises hydrogen.

In one particular embodiment, the composition contains an ethoxylated lauryl alcohol. The ethoxylated lauryl alcohol can contain from about 6 mols to about 15 mols of ethoxylate, such as from about 7 mols to about 10 mols of ethoxylate.

Other non-ionic surfactants that may be used in the composition include, but are not limited to, polyoxyethylene glycol alkyl ethers, octaethylene glycol monododecyl ether, pentaethylene glycol monododecyl ether, polyoxypropylene glycol alkyl ethers, glucoside alkyl ethers, decyl glucoside, lauryl glucoside, octyl glucoside, polyoxyethylene glycol octylphenol ethers, polyoxyethylene glycol alkylphenol ethers, glycerol alkyl esters, polyglycerol esters, glyceryl laurate, polyoxyethylene glycol sorbitan alkyl esters, sorbitan alkyl esters, dodecyldimethylamine oxide, block copolymers of polyethylene glycol and polypropylene glycol, poloxamers and polyethoxylated tallow amine (POEA), and mixtures thereof.

Additionally, the disinfectant product may contain an optional chelating agent. Chelating agents include, for example, an acetic acid derivative selected from the group consisting of ethylenediaminetetraacetic acid (EDTA), nitrilotriacetic acid (NTA), tetrasodium EDTA. The chelating agent may serve to bind other metal ions that may adversely affect the effectiveness of the disinfecting components in the composition. In addition, chelating agents may also assist in soil removal and/or preventing soil redeposition into the disinfecting composition while in use. The chelating agents, when present in the composition are generally present in an amount up to about 20% by weight, and are typically present in an amount of about 0.05% to about 8% by weight.

The disinfectant composition may also contain a pH adjusting agent. Suitable pH adjusting agents include sodium hydroxide, sodium citrate and other similar compounds. The disinfectant composition will have a pH in the range of about 6 to about 13. Generally the disinfectant composition will be considered a neutral disinfecting composition if the pH is in the range of about 6 to about 8. The disinfectant composition will be considered an alkaline disinfectant composition when the pH is in the range of above 8 to about 12.

The disinfectant composition may optionally further contain corrosion inhibitors, complexing agents, auxiliaries, preservatives, fragrances, colorants and the like. Exemplary corrosion inhibitors include, for example, organic phosphorous compounds and blend of organic phosphorous compounds with a polymeric component. Colorants and fragrances may be added provided they do not interfere with the function of the composition and may serve for identifying the composition. Generally, the optional further ingredients will make up less than about 20% by weight of the composition.

Various different microorganisms may be killed or controlled in accordance with the present disclosure. For instance, the antimicrobial composition of the present disclosure can control gram positive bacteria, gram negative bacteria, and the like. In addition to bacteria, the antimicrobial composition of the present disclosure can also kill and control the growth of various other microorganisms, such as fungi, viruses, spores, yeast, mycobacteria, and the like. Examples of particular microorganisms that may be killed or controlled in accordance with the present disclosure include *Staphylococcus aureus, Streptococcus pneumoniae, Pseudomonas aeruginosa, Serratia marcescens, Salmonella ententidis, Neisseria gonorrhoeae, Escherichia coli, Enterococcus hirae, Acinetobacter baumannii, Listeria monocytogenes, Enterobacter gergoviae, Klebsiella pneumoniae, Burholderia cepacia, Pseudomonas putida, Kocuria rhizophila, Candida albicans, Saccharomyces cerevisiae, Aspergillus brasiliensis, Penicillium funiculosum, Eupenicillium levitum, Bacillus cereus, Bacillus subtilis, Clostridium difficile, Clostridium perfringens, Mycobacterium tuberculosis, Mycobacterium terrae, Mycobacterium avium,* Poliovirus, Adenovirus, Norovirus, Vaccinia virus, Influenza virus, Hepatitis B virus, Human Immunodeficiency virus, Human papilloma virus, or mixtures thereof.

Various different disinfectant products can be made in accordance with the present disclosure. The disinfectant product may be used, for instance, to clean hard surfaces, to pre-clean sterilize or high-level disinfect instruments, and/or as a hand sanitizer.

When used as a hard surface cleaner, the disinfectant composition can be delivered to a surface to be cleaned, sanitized or disinfected by conventional means such as pouring the composition on a surface; a spray; which is applied to a surface via a spray means, including but not limited to, pump spray applicators, pressurized spray applicators and the like; a saturated wipe; a rag and a bucket; a mop and bucket; a sponge and a bucket; or via automated cleaning equipment and other similar and conventional ways to apply an anti-microbial or disinfectant composition to a surface for the purposes of sanitizing or disinfecting the surface.

To use the disinfectant composition of the present disclosure, a surface is treated with the substrate by spraying, pouring, wiping or otherwise applying the anti-microbial composition to the surface. Once applied to the surface, the anti-microbial composition is allowed to remain on the surface for a period of time. The anti-microbial composition may be applied to the surface and allowed to dry or may alternatively be dried by wiping the surface with a dry wipe or wiping device.

Surfaces, which may be disinfected with the compositions include, but are not limited to, those located in dairies, homes, health care facilities, swimming pools, canneries, food processing plants, restaurants, hospitals, institutions, and industry, including secondary oil recovery. Any suitable hard surface may be treated in accordance with the present disclosure, particularly frequently touched hard surfaces. The hard surface, for instance, can be made from glass, a metal such as an aluminum or stainless steel, a ceramic, a stone such as granite or marble, a plastic or polymer material, or the like. Specific areas targeted for application include hard surfaces in the home such as kitchen countertops, cabinets, appliances, waste cans, laundry areas, garbage pails, bathroom fixtures, toilets, water tanks, faucets, mirrors, vanities, tubs, and showers. The compositions can also be used to sanitize floors, walls, furniture, mirrors, toilet fixtures, windows, and wood surfaces, such as fence rails, porch rails, decks, roofing, siding, window frames, and door frames. The compositions are particularly well suited for application on indirect food contact surfaces, such as cutting boards, utensils, containers, dishes, wash basins, appliances, and countertops. The compositions can be used to sanitize dairy plant equipment, milking machines, milk pails, tank trucks, and the like. Areas in hospitals would include beds, gurneys, tables, canisters, toilets, waste cans, stands, cabinets, shower stalls, floors, door knobs, bed rails, walls or any other non-porous surface.

One particularly useful application method is to impregnate the disinfectant composition into a wipe substrate. In this embodiment, the wipe can be a single use wipe that is impregnated with the disinfecting composition and is stored in a container that will dispense the wipe to a user. The container with the wipes may contain a single wipe, or several wipes. Suitable containers include a pouch containing a single wipe, such as a moist towelette which is torn open by the user, or may be a pouch with a resealable opening containing several wipes in a stacked fashion, a rolled fashion or other suitable formation that would allow a single wipe to be removed from the opening at a time. Pouches are generally prepared from a fluid impervious material, such as a film, a coated paper or foil or other similar fluid impervious materials. Another way to dispense wipes of the present disclosure is to place the wipe in to a fluid impervious container having an opening to access the wipes in the container. Containers may be molded plastic containers with lids that are fluid impervious. Generally, the lid will have an opening to access the wipes in the container. The wipe in the container may be in a interleaved stacked, such that as a wipe is removed from the container the next wipe is positioned in the opening of the container ready for the user to remove the next wipe. Alternatively, the wipe may be a continuous material which is perforated between the individual wipes of the continuous material. The continuous wipe material with perforations may be in a folded form or may be in a rolled form. Generally, in the rolled form, the wipe material is feed from the center of the rolled material. As with the interleaved stack, as a wipe is removed from the container, the next wipe is positioned in the opening for the use to remove the next wipe, when needed.

The disinfecting composition can be impregnated into the wipe such that the wipe is pre-moistened and will express or release the disinfecting composition onto the surface as the wipe is run across the surface to be treated. Generally, the disinfecting composition is saturated into the wipe such that the wipe will release the disinfecting composition onto the surface through the wiping action. Depending on the wipe substrate, saturation is generally achieved using about 3 wt parts of the disinfecting composition per 1 wt part of the wipe substrate to be saturated. Generally, the disinfecting composition is used from about 4 parts to 6 parts by weight per 1 part by weight of the wiper substrate. In these ranges, complete saturation of the substrates can be achieved. It is noted that the amount of the disinfecting solution may go up or down to achieve complete saturation of the wipe substrate, depending on the particular wipe substrate.

Suitable wipe substrates include woven and nonwoven materials. Essentially any nonwoven web material may be used. Exemplary nonwoven materials may include, but are not limited to meltblown, coform, spunbond, airlaid, hydroentangled nonwovens, spunlace, bonded carded webs, and laminates thereof. Optionally, the nonwoven may be laminated with a film material as well. The fibers used to prepare the wipe substrate may be cellulosic fiber, thermoplastic fibers and mixtures thereof. The fibers may also be continuous fibers, discontinuous fibers, staple fibers and mixtures thereof. Basis weights of the nonwoven web may vary from about 12 grams per square meter to 200 grams per square meter or more.

The present disclosure may be better understood with reference to the following examples.

Example No. 1

1. Formulation Preparation
1.1. Polymer Base Formulations

The base formulations were prepared using different polymers and different levels of isopropyl alcohol as shown in Table 1. The polymer base formulations were mixed at room temperature, except for the base formulations containing polyvinyl alcohols (PVOH), which was prepared by mixing the ingredients and stirring at 50-60° C. until the PVOH was completely dissolved. The base formulations were cooled to room temperature before they were further formulated with the biocides.

TABLE 1

Polymer base formulations

| Ingredients | A | B | C | D | E | F | G | H |
|---|---|---|---|---|---|---|---|---|
| PVOH-98[1] | 5.2 | | | | | 3.4 | 3.4 | 3.4 |
| PVOH-96[2] | | 5.2 | | | | 1.8 | 1.8 | 1.8 |
| PVP[3] K-60 | | | 5.2 | | | | | |
| PVP K-90 | | | | 5.2 | | | | |
| Polyethylene glycol (PEG) (3350 Mn) | | | | | 5.2 | | | |
| Isopropyl alcohol | 19.2 | 19.2 | 19.2 | 19.2 | 19.2 | 19.2 | 5.26 | 0 |
| DI water | 75.6 | 75.6 | 75.6 | 75.6 | 75.6 | 75.6 | 89.54 | 94.8 |
| Total | 100 | 100 | 100 | 100 | 100 | 100 | 100 | 100 |

[1]Polyvinyl alcohol 98% hydrolyzed
[2]Polyvinyl alcohol 96% hydrolyzed
[3]Polyvinylpyrrolidone

TABLE 2

Examples of biocide/polymer formulations

| | Formulations | | | | | |
|---|---|---|---|---|---|---|
| | A % w/w | B % w/w | C % w/w | D % w/w | E % w/w | F % w/w |
| Polymer base formulation A | 95.0 | 95.0 | 95.0 | 95.0 | | |
| Polymer base formulation F | | | | | 95.0 | |
| Polymer base formulation H | | | | | | 95.0 |
| Alkyldimethyl benzyl ammonium chlorides | 0.5 | | | | | |
| N,N-bis(3-aminopropyl) dodecylamine | | 0.4 | | | 0.4 | 0.4 |
| Chlorhexidine digluconate | | | 0.4 | | | |
| PHMB | | | | 2.0 | | 0.5 |
| Na₄ EDTA | | | | | | 0.1 |
| DI water | 4.5 | 4.6 | 3.0 | 4.6 | 4.6 | 4.0 |
| Total | 100 | 100 | 100 | 100 | 100 | 100 |

1.2. Biocide/Polymer Based Formulations

A biocide/polymer formulation was prepared by adding biocides into the polymer base formulations. Examples of biocide/polymer formulations in Table 2 contained 0.4% active biocides.

2. Micro-Efficacy Testing

First round of micro test was to evaluate the efficacy of the biocides against *P. aeruginosa*. About 30 mg of the biocide/polymer based formulation were coated on the one square inch area of a stainless steel coupon. The treated stainless steel coupons were left on the bench for air drying overnight. The dried stainless steel test samples were sent to a micro lab for efficacy testing against *P. aeruginosa* ATCC 15442 following a modified version of Residual Self-Sanitizing Activity on Hard, Non-Porous Surfaces (EPA Protocol #01-1A). Test samples did not undergo the wearing process. Samples were inoculated with the test organism and held for a 5 minute contact time. Three replicates were tested for each sample. Test results are shown in Table 3.

TABLE 3

First screening test results - average log reduction against *P. aeruginosa*

| Actives | Active concentration (%) | Film | Log reduction (with culture dilution) |
|---|---|---|---|
| Alkyldimethyl benzyl ammonium chlorides | 0.4 | PVOH | 3.85 |
| N,N-bis(3-aminopropyl) dodecylamine | 0.4 | PVOH | ≥4.85 |
| N,N-bis(3-aminopropyl) dodecylamine | 0.4 | PVP | 4.05 |
| Chlorhexidine digluconate | 1.0 | PVOH | ≥4.85 |
| PHMB | 0.4 | PVOH | 3.56 |

Second round of testing was to compare the efficacy after an abrasion process. About 30 mg of the test formulation was coated on the one square inch area of a stainless steel coupon. Samples were divided into two groups: one group had 0 rub, and the other group had 12 dry rubs. No re-inoculation was applied between rubs. Test results are shown in Table 4.

TABLE 4

Second screening test results - average log reduction against *P. aeruginosa*

| | | | $Log_{10}$ Reduction | |
|---|---|---|---|---|
| Formulations | Active % | Film | No Rub | 12 dry Rubs |
| Alkyldimethyl benzyl ammonium chlorides | 0.4 | PVOH | 3.56 | 3.48 |
| N,N-bis(3-aminopropyl) dodecylamine | 0.4 | PVOH | 5.22 | 4.77 |
| Chlorhexidine digluconate | 0.4 | PVOH | 5.42 | 5.04 |
| PHMB | 0.4 | PVOH | 1.97 | 2.24 |

Third round of testing was to evaluate the N,N-bis(3-aminopropyl) dodecylamine/PVOH based formulation for residual efficacy against *P. aeruginosa* and *S. Aureus* at two loadings of 30 mg and 10 mg. Samples were divided into three groups for different wearing procedures: the first group had 0 rub; the second group had 12 dry rubs, and the third group had 12 wet rubs. No re-inoculation was applied between rubs. Test results are shown in Table 5-6. Performance standard for passing the self-sanitation test is 3 log reduction.

TABLE 5

Third screening test results - average log reduction against *S. aureus*

| | | $Log_{10}$ Reduction | | | | | |
|---|---|---|---|---|---|---|---|
| | | Film Thickness 30 mg | | | Film Thickness 10 mg | | |
| Formulations | Active % | No Rub | 12 Dry Rubs | 12 Wet Rubs | No Rub | 12 Dry Rubs | 12 Wet Rubs |
| N,N-bis(3-aminopropyl) dodecylamine/ PVOH | 0.4 | >4.82 | 4.63 | >4.87 | 4.09 | 4.08 | 4.06 |

TABLE 6

Third screening test results - average log reduction against *P. aeruginosa*

| | | Log₁₀ Reduction | | | | | |
|---|---|---|---|---|---|---|---|
| | | Film Thickness 30 mg | | | Film Thickness 10 mg | | |
| Formulations | Active % | No Rub | 12 Dry Rubs | 12 Wet Rubs | No Rub | 12 Dry Rubs | 12 Wet Rubs |
| N,N-bis(3-aminopropyl) dodecylamine/ PVOH | 0.4 | 4.18 | >4.94 | >4.89 | >4.96 | >4.94 | 3.82 |

The N, N-bis(3-aminopropyl) dodecylamine/PVOH based formulation was also tested for 8 and 12 hour residual efficacy using the Protocol for Residual Self-Sanitizing Activity of Dried Chemical Residues on Hard, Non-Porous Surfaces (EPA Protocol #01-1A) with proportional reduction of abrasion numbers and inoculation numbers. The formulation details are shown in Table 7 and residual efficacy test results are shown in Table 8.

TABLE 7

N,N-bis(3-aminopropyl) dodecylamine/PVOH formulation recipe

| Ingredients | % w/w |
|---|---|
| N,N-bis(3-aminopropyl) dodecylamine | 0.4 |
| PVOH-98 | 3.3 |
| PVOH-96 | 1.7 |
| Isopropyl alcohol | 18.0 |
| DI water | 76.6 |

TABLE 8

Residual test results using EPA Protocol #01-1A

| | | Test conditions | | | Log Reduction* | | |
|---|---|---|---|---|---|---|---|
| Residual hours | Contact time | Dry rub | Wet Rub | Reinoculation | S. aureus | P. aeruginosa | E. aerogenes |
| 8 hrs | 10 | 2 | 2 | 3 | 4.90 | | |
| | 5 | 2 | 2 | 3 | | 5.49 | 3.72 |
| 12 hrs | 5 | 3 | 3 | 3 | 3.57 | 5.57 | |

*Performance standard for passing the self-sanitation test is ≥3 log reduction.

The initial efficacy against *Staphylococcus aureus* ATCC 6538 and *Pseudomonas aeruginosa* ATCC 15442 for the same N, N-bis(3-aminopropyl) dodecylamine/PVOH formulation was also confirmed using the AOAC Germicidal Spray Test method (961.02). The test results are shown in Table 9,

TABLE 9

Initial efficacy test results

| Formulation | Contact time | Organism | Positive Carriers* |
|---|---|---|---|
| N,N-bis(3-aminopropyl) dodecylamine/ PVOH | 5 min. | S. aureus | 0/60 Passed |
| | 5 min. | P. aeruginosa | 0/60 Passed |

*Performance standard for passing is ≤1 positive carrier out of 60.

Example No. 2

The following biocides/polymer formulations were also prepared and tested:

TABLE 10

| Ingredients | Sample No. 1 % w/w | Sample No. 2 % w/w |
|---|---|---|
| N,N-bis(3-aminopropyl) dodecylamine | 1.5 | 1.2 |
| POVH-98 | 1.5 | 2.0 |
| Polyvinylpyrrolidone | 1.5 | 1.0 |
| Isopropyl alcohol | 15.0 | 15.0 |
| DI water | q.s. to 100 | q.s. to 100 |

The polyvinyl alcohol used above had an average molecular weight of 125 kg/mol. The polyvinylpyrrolidone used above had an average molecular weight of from about 1000 to about 1700 kg/mol.

Formulations in Table 10 were submitted to a micro lab for residual efficacy test following the EPA New Guideline for Residual Antimicrobial Activity of Dried Chemical on Hard Non-Porous Surfaces as described above. Each abrasion equals four (4) passes (one pass to the left and one return pass to the right followed by another pass to the left and another return pass to the right); each cycle is composed of inoculation or re-inoculation followed by one wet abrasion or one dry abrasion. A minimum of 4 hours bacterial reduction claim is acceptable. Each 4 hour increment represents one dry abrasion cycle and one wet abrasion cycle with inoculation or re-inoculation. A 1 inch by 3 inch glass microscope slide was used as a test carrier in the residual test. The test results are shown in Table 11. Both formulations demonstrated 4 hour residual disinfection against both *S. aureus* and *P. aeruginosa* with greater than 5 log reduction.

TABLE 11

Residual test results using modified Clorox method

| Residual hours | Sample No. | Contact time | Log Reduction* S. aureus | P. aeruginosa |
|---|---|---|---|---|
| 4 hrs | 1 | 10 | >5.14 | >5.20 |
|  | 2 | 5 | >5.35 | >5.26 |

The initial efficacy for the formulations in Table 10 against *Staphylococcus aureus* ATCC 6538 and *Pseudomonas aeruginosa* ATCC 15442 for the same formulations were also confirmed using the AOAC Germicidal Spray Test method (961.02). The test results are shown in Table 12.

TABLE 12

Initial efficacy test results

| Sample No. | Contact time | Organism | Positive Carriers* |
|---|---|---|---|
| 1 | 5 min. | S. aureus | 0/60 Passed |
|  | 5 min. | P. aeruginosa | 0/60 Passed |
| 2 | 5 min | S. aureus | 0/60 Passed |
|  | 5 min | P. aeruginosa | 0/60 Passed |

*Performance standard for passing is ≤1 positive carrier out of 60.

Example No. 3

As shown above, compositions made in accordance with the present disclosure demonstrate excellent initial antimicrobial activity, are abrasion resistant, and have prolonged antimicrobial activity. The following are further formulations made in accordance with the present disclosure and would also demonstrate similar results.

TABLE 13

More N,N-bis(3-aminopropyl) dodecylamine/PVOH based formulations for micro residual efficacy testing against S. aureus, E. aerogenes and P. aeruginosa

| Ingredients | A (% w/w) | B (% w/w) | C (% w/w) |
|---|---|---|---|
| N,N-bis(3-aminopropyl) dodecylamine | 0.4 | 0.4 | 0.4 |
| PHMB | — | 0.1 | 0.1 |
| PVOH-98 | 3.3 | 3.3 | 3.3 |
| PVOH-96 | 1.7 | 1.7 | 1.7 |
| Na$_4$EDTA | 0.1 | — | — |
| Nonionic ethoxylated C$_{12}$ C$_{14}$ alcohol containing 9 mols of ethoxylate | — | 0.1 | — |
| Isopropyl alcohol | — | — | 0.95 |
| DI water | 94.5 | 94.4 | 93.55 |

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A composition for disinfecting surfaces comprising:
   a biocide, the biocide comprising a tertiary amine biocide, a chlorhexidine, a biguanide, or mixtures thereof;
   a film forming component combined with the biocide, the film forming component comprising a polyvinyl alcohol having a degree of hydrolysis of greater than about 90 mol %, a polyvinyl pyrrolidone, a polyalkylene glycol, or mixtures thereof; and
   a liquid carrier.

2. A composition as defined in claim 1, wherein the biocide comprises the tertiary amine biocide.

3. A composition as defined in claim 2, wherein tertiary amine comprises a tertiary alkyl amine.

4. A composition as defined in claim 2, wherein the biocide is N, N-bis(3-aminopropyl) dodecylamine, N-(3-aminopropyl)-N-dodecylpropane-1,3-diamine, N-(3-aminopropyl)-N-decyl-1,3-propanediamine, N-(3-aminopropyl)-N-tetradecyl-1,3-propanediamine, or mixtures thereof.

5. A composition as defined in claim 1, wherein the biocide is present in the composition in an about from about 0.1% to about 2% by weight.

6. A composition as defined in claim 1, wherein the film forming component comprises the polyvinyl alcohol.

7. A composition as defined in claim 6, wherein the polyvinyl alcohol has a degree of hydrolysis of greater than about 95 mol %.

8. A composition as defined in claim 6, wherein the composition contains a first polyvinyl alcohol and a second polyvinyl alcohol, the first polyvinyl alcohol having a degree of hydrolysis greater than the second polyvinyl alcohol, the first polyvinyl alcohol and the second polyvinyl alcohol both having a degree of hydrolysis of greater than about 90 mol %.

9. A composition as defined in claim 8, wherein the first polyvinyl alcohol has a degree of hydrolysis of about 98 mol % and the second polyvinyl alcohol has a degree of hydrolysis of from about 95 mol % to about 97 mol %, the first polyvinyl alcohol and the second polyvinyl alcohol being present in the composition at a weight ratio of from about 1:1 to about 4:1.

10. A composition as defined in claim 1, wherein the film forming component is present in the composition in an amount from about 1% to about 10% by weight.

11. A composition as defined in claim 1, wherein the liquid carrier comprises water, water being present in the composition in an amount of at least 40% by weight.

12. A composition as defined in claim 1, wherein the composition further contains an evaporating agent, the evaporating agent having a boiling point of less than about 90° C.

13. A composition as defined in claim 12, wherein the evaporating agent comprises an alcohol.

14. A composition as defined in claim 12, wherein the evaporating agent is present in the composition in an amount from about 1% to about 25%.

15. A composition as defined in claim 1, wherein the film forming component comprises the polyvinyl pyrrolidone.

16. A composition as defined in claim 1, wherein the composition further contains a chelating agent.

17. A composition as defined in claim 1, wherein the composition further contains a surfactant.

18. A composition as defined in claim 1, wherein the biocide comprises the chlorhexidine, the chlorhexidine comprising chlorhexidine digluconate.

19. A composition as defined in claim 1, wherein the biocide comprises the biguanide, the biguanide comprising a polyhexamethylene biguanide hydrochloride.

20. A composition as defined in claim 1, wherein the biocide comprises the tertiary amine biocide in combination with a chlorhexidine or a biguanide.

21. A premoistened wiper comprising a liquid absorbent substrate impregnated with the composition as defined in claim 1.

22. A disinfectant product for disinfecting instruments comprising the composition as defined in claim 1.

23. A hard surfaces disinfectant comprising the composition as defined in claim 1.

24. A hand sanitizer comprising the composition as defined in claim 1.

* * * * *